(12) United States Patent
Buljubasic

(10) Patent No.: US 11,324,533 B2
(45) Date of Patent: May 10, 2022

(54) SYSTEMS AND METHODS FOR PROVIDING ULTRASOUND GUIDANCE TO TARGET STRUCTURES WITHIN A BODY

(71) Applicant: Neda Buljubasic, Los Angeles, CA (US)

(72) Inventor: Neda Buljubasic, Los Angeles, CA (US)

( * ) Notice: Subject to any disclaimer, the term of this patent is extended or adjusted under 35 U.S.C. 154(b) by 274 days.

(21) Appl. No.: 16/353,692

(22) Filed: Mar. 14, 2019

(65) Prior Publication Data

US 2019/0209207 A1 Jul. 11, 2019

Related U.S. Application Data

(62) Division of application No. 15/253,673, filed on Aug. 31, 2016, now Pat. No. 10,806,486.

(Continued)

(51) Int. Cl.
*A61B 8/14* (2006.01)
*A61B 17/34* (2006.01)
(Continued)

(52) U.S. Cl.
CPC ...... *A61B 17/3403* (2013.01); *A61B 5/15003* (2013.01); *A61B 5/150748* (2013.01); *A61B 8/0841* (2013.01); *A61B 8/4209* (2013.01); *A61B 8/4494* (2013.01); *A61B 8/483* (2013.01); *A61B 46/10* (2016.02); *A61B 90/13* (2016.02); *A61M 5/427* (2013.01); *A61B 8/4455* (2013.01);

(Continued)

(58) Field of Classification Search
IPC .............. A61B 5/15003,8/0841, 8/4209, 8/483, 17/3403
See application file for complete search history.

(56) References Cited

U.S. PATENT DOCUMENTS

| | | | |
|---|---|---|---|
| 5,891,158 A | 4/1999 | Manwaring et al. | |
| 5,976,092 A | 11/1999 | Chinn | |

(Continued)

FOREIGN PATENT DOCUMENTS

| | | |
|---|---|---|
| CN | 102551797 | 7/2012 |
| CN | 202553984 | 11/2012 |

(Continued)

*Primary Examiner* — Joel F Brutus
(74) *Attorney, Agent, or Firm* — Sheppard, Mullin, Richter & Hampton LLP

(57) ABSTRACT

An ultrasonic probe comprising a housing, a first ultrasonic transducer array, a second ultrasonic transducer array, a first light source, and a second light source. The first ultrasonic transducer array is coupled to the housing and configured to emit a first planar ultrasonic beam in a first direction within a first plane. The second ultrasonic transducer array is coupled to the housing and configured to emit a second planar ultrasonic beam in the first direction within a second plane, which is substantially perpendicular to the first plane. The first light source is coupled to the housing and configured to project a first light line substantially within the first plane. The second light source is coupled to the housing and configured to project a second light line within a third plane, which is substantially perpendicular to the first plane and intersects the second plane at an oblique angle. The first light line intersects and is substantially perpendicular to the second light line.

16 Claims, 17 Drawing Sheets

Related U.S. Application Data

(60) Provisional application No. 62/212,586, filed on Aug. 31, 2015.

(51) Int. Cl.

| | |
|---|---|
| *A61B 8/08* | (2006.01) |
| *A61B 8/00* | (2006.01) |
| *A61B 46/10* | (2016.01) |
| *A61B 90/13* | (2016.01) |
| *A61M 5/42* | (2006.01) |
| *A61B 5/15* | (2006.01) |
| *G01S 15/89* | (2006.01) |
| *A61M 25/01* | (2006.01) |
| *A61B 18/20* | (2006.01) |
| *A61B 90/00* | (2016.01) |

(52) U.S. Cl.
CPC .............. *A61B 8/4477* (2013.01); *A61B 8/463* (2013.01); *A61B 8/467* (2013.01); *A61B 8/54* (2013.01); *A61B 2017/3413* (2013.01); *A61B 2018/2025* (2013.01); *A61B 2090/0811* (2016.02); *A61B 2090/378* (2016.02); *A61M 25/01* (2013.01); *G01S 15/899* (2013.01)

(56) References Cited

U.S. PATENT DOCUMENTS

| | | |
|---|---|---|
| 6,702,749 B2 | 3/2004 | Paladini et al. |
| 6,755,789 B2 | 6/2004 | Stringer et al. |
| 8,118,743 B2 | 2/2012 | Park et al. |
| 8,162,852 B2 | 4/2012 | Norris |
| 2003/0120154 A1* | 6/2003 | Sauer .................. A61B 8/0833 600/459 |
| 2010/0041996 A1 | 2/2010 | Nygaard et al. |
| 2012/0095339 A1 | 4/2012 | Tashiro |
| 2013/0016185 A1 | 1/2013 | Stolka et al. |
| 2013/0190591 A1 | 7/2013 | Hirson et al. |
| 2014/0031674 A1 | 1/2014 | Newman et al. |
| 2015/0038825 A1 | 2/2015 | Abe |
| 2015/0080740 A1 | 3/2015 | Hao et al. |
| 2015/0148664 A1 | 5/2015 | Stolka et al. |
| 2015/0230776 A1 | 8/2015 | Meier |

FOREIGN PATENT DOCUMENTS

| | | |
|---|---|---|
| CN | 202801811 | 3/2013 |
| CN | 103347449 | 10/2013 |
| CN | 104244837 | 12/2014 |
| CN | 103222897 | 6/2015 |
| CN | 105232120 | 1/2016 |
| JP | 2004135693 | 5/2004 |
| JP | 2009045427 | 3/2009 |
| JP | 2012081134 | 4/2012 |

* cited by examiner

SYSTEMS AND METHODS FOR PROVIDING ULTRASOUND GUIDANCE TO TARGET STRUCTURES WITHIN A BODY

CROSS-REFERENCE TO RELATED APPLICATIONS

This application is a divisional of U.S. patent application Ser. No. 15/253,673, filed on Aug. 31, 2016, which claims the benefit of U.S. Provisional Patent Application No. 62/212,586, filed on Aug. 31, 2015, which is incorporated by reference in its entirety.

FIELD OF THE INVENTION

This invention relates generally to ultrasound probes and, more particularly, to an ultrasound probe having guidance light sources and methods of directing an instrument from a surface to a target structure beneath the surface.

BACKGROUND

Ultrasound is a medical imaging tool that, in certain implementations, permits health care practitioners to locate and visualize internal bodily structures, such as blood vessels and internal organs. When these internal structures need to be accessed, ultrasound is sometimes used to direct an instrument toward the target structure. For example, ultrasound may be used for to assist with venous line placement, arterial line placement, biopsy, drainage, ablation, or other interventions.

Unfortunately, despite the improvements in ultrasound technology, as well as training and operator skills, it is still difficult to reliably and continuously direct the instrument to the target structure without complications. While an improvement over unguided approaches, current ultrasound probes are still limited in the guidance that they provide.

It should be appreciated that there is a need for an ultrasound probe that enables heath care practitioners to safely perform procedures involving internal bodily structures with greater ease and accuracy and fewer complications. The probe should reliably and continuously direct an instrument from a surface to a target structure beneath the surface. The present invention fulfills these needs and provides further related advantages.

BRIEF SUMMARY OF THE INVENTION

The present invention is embodied in an ultrasonic probe, which includes a housing, a first ultrasonic transducer array, a second ultrasonic transducer array, a first light source, and a second light source. The first ultrasonic transducer array is coupled to the housing and configured to emit a first planar ultrasonic beam in a first direction within a first plane. The second ultrasonic transducer array is coupled to the housing and configured to emit a second planar ultrasonic beam in the first direction within a second plane, which is substantially perpendicular to the first plane. The first light source is coupled to the housing and configured to project a first light line substantially within the first plane. The second light source is coupled to the housing and configured to project a second light line within a third plane, which is substantially perpendicular to the first plane and intersects the second plane at an oblique angle. The first light line intersects and is substantially perpendicular to the second light line.

In one embodiment, the ultrasound probe is embodied in a handheld device. In another embodiment, the first and second ultrasonic transducer arrays are arranged in a T-shaped configuration.

In one embodiment, the first light source is a first laser and the second light source is a second laser. In another embodiment, the second laser is configured to project the second light line within the third plane at a projection angle, wherein the projection angle is less than 90°. In an additional embodiment, a stepper motor coupled to the second laser. In a further embodiment, the stepper motor is configured to rotate the second laser and thereby adjust the projection angle, wherein the adjusted projection angle is less than 90°. In yet another embodiment, a position of the second laser relative to the first laser is adjustable.

In one embodiment, the ultrasound probe further includes a control panel. In another embodiment, the control panel includes a touch screen. In a further embodiment, the ultrasound probe includes a screen coupled to the ultrasound probe and configured to display both a first image from the first ultrasonic transducer array and a second image from the second ultrasonic transducer array. In an additional embodiment, the screen is configured to display a centerline. In another embodiment, the centerline corresponds to a center of the second ultrasonic transducer array. In yet another embodiment, the centerline corresponds to a point of intersection between the first ultrasonic transducer array and the second ultrasonic transducer array.

In one embodiment, the ultrasound probe further comprises a sterile cover coupled to the ultrasonic probe. In another embodiment, the sterile cover comprises a rigid, optically transparent material configured to be positioned over the first and second light source. In a further embodiment, the sterile cover further comprises a flexible bag coupled to the rigid, optically transparent material.

The present invention is also embodied in a method of directing an instrument from a surface to a target structure beneath the surface. In one embodiment, the method includes emitting a first planar ultrasonic beam in a first direction within a first plane, emitting a second planar ultrasonic beam in the first direction within a second plane, projecting a first light line substantially within the first plane, projecting a second light line within a third plane, aligning an end of the instrument with a point of entry, aligning a length of the instrument with both a guide path and an angle of entry, and guiding the instrument through the point of entry toward the target structure beneath the surface, while substantially maintaining alignment of the length of the instrument with both the guide path and the angle of entry. The second plane and the third plane are both substantially perpendicular to the first plane. The third plane intersects the second plane at an oblique angle and defines the angle of entry for the instrument. The first light line defines the guide path for the instrument. The second light line intersects and is substantially perpendicular to the first light line, and a point of intersection between the first light line and the second light line defines the point of entry for the instrument.

In one embodiment, the method includes displaying both a first image from the first planar ultrasonic beam and a second image from the second planar ultrasonic beam. In a further embodiment, the second image includes a centerline. In another embodiment, the centerline corresponds to a center of the second planar ultrasonic beam. In yet another embodiment, the centerline corresponds to a point of intersection between the first planar ultrasonic beam and the second planar ultrasonic beam.

In one embodiment, the method includes aligning the second planar ultrasonic beam over the target structure such that the centerline of the second image is substantially centered over the image of the target structure. In another embodiment, the method includes aligning the first planar ultrasonic beam over the target structure such that the target structure is visible in the first image while the centerline of the second image is substantially centered over the target structure.

In another embodiment, the method includes selecting the target structure on the first or second image. In a further embodiment, the method includes selecting a desired angle of entry. In an additional embodiment, the method includes selecting a desired point of entry on the first image. In yet another embodiment, the method includes selecting both a desired point of entry on the first image and a desired angle of entry.

In one embodiment, the method includes determining both a vertical and a horizontal distance between the target structure and a light source projecting the second light line. In one embodiment, the method includes calculating a projection angle of the light source required to project the second light line within the third plane such that the third plane is substantially incident a point of intersection between the second plane and the target structure. The projection angle is defined by the equation $\alpha = \arctan(y/x)$, where $\alpha$ is the projection angle, y is the vertical distance between the target structure and the light source, and x is the horizontal distance between the target structure and the light source. In another embodiment, the method includes rotating the light source so as to project the second light line within the third plane substantially at the calculated projection angle.

In one embodiment, the method includes calculating a position of the light source required to project the second light line within the third plane such that the third plane is substantially incident a point of intersection between the second plane and the target structure. The position is determined from an equation $\tan \alpha = y/x$, where $\alpha$ is a projection angle of the light source, y is the vertical distance between the target structure and the light source, and x is the horizontal distance between the target structure and the light source. In another embodiment, the method includes moving the light source substantially to the calculated position.

In one embodiment, the method includes the step of calculating both a projection angle and a position of the light source required to project the second light line within the third plane such that the third plane is substantially incident a point of intersection between the second plane and the target structure. The projection angle and position are determined from an equation $\tan \alpha = y/x$, where $\alpha$ is the projection angle, y is the vertical distance between the target structure and the light source, and x is the horizontal distance between the target structure and the light source. In another embodiment, the method includes rotating the light source so as to project the second light line within the third plane substantially at the calculated projection angle, and moving the light source substantially to the calculated position.

Other features and advantages of the invention should become apparent from the following description of the preferred embodiments, taken in conjunction with the accompanying drawings, which illustrate, by way of example, the principles of the invention.

DETAILED DESCRIPTION OF THE PREFERRED EMBODIMENTS

Figure 1:
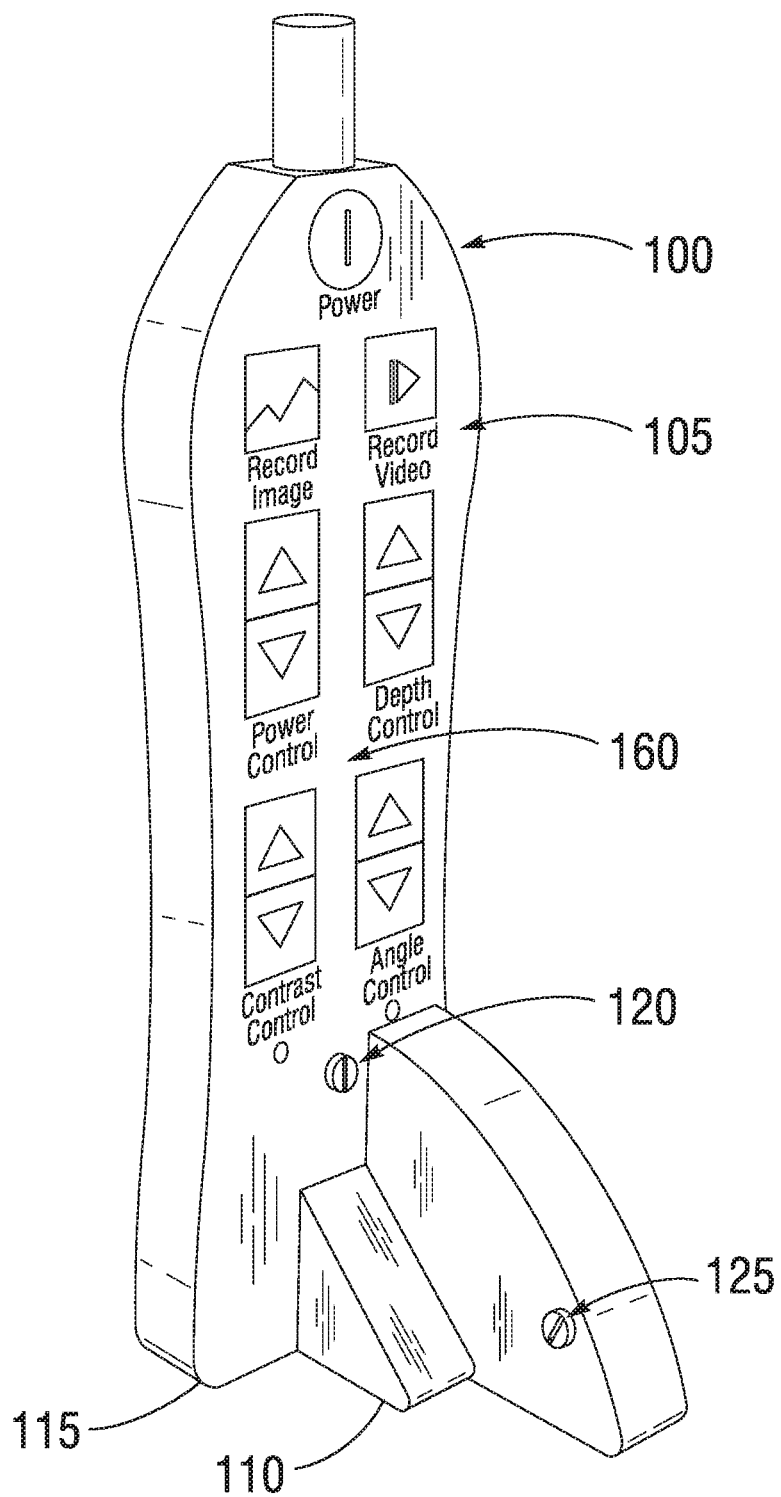
FIG. 1 is a top-left perspective view of an ultrasound probe in accordance with one embodiment of the present invention.
Figure 2:
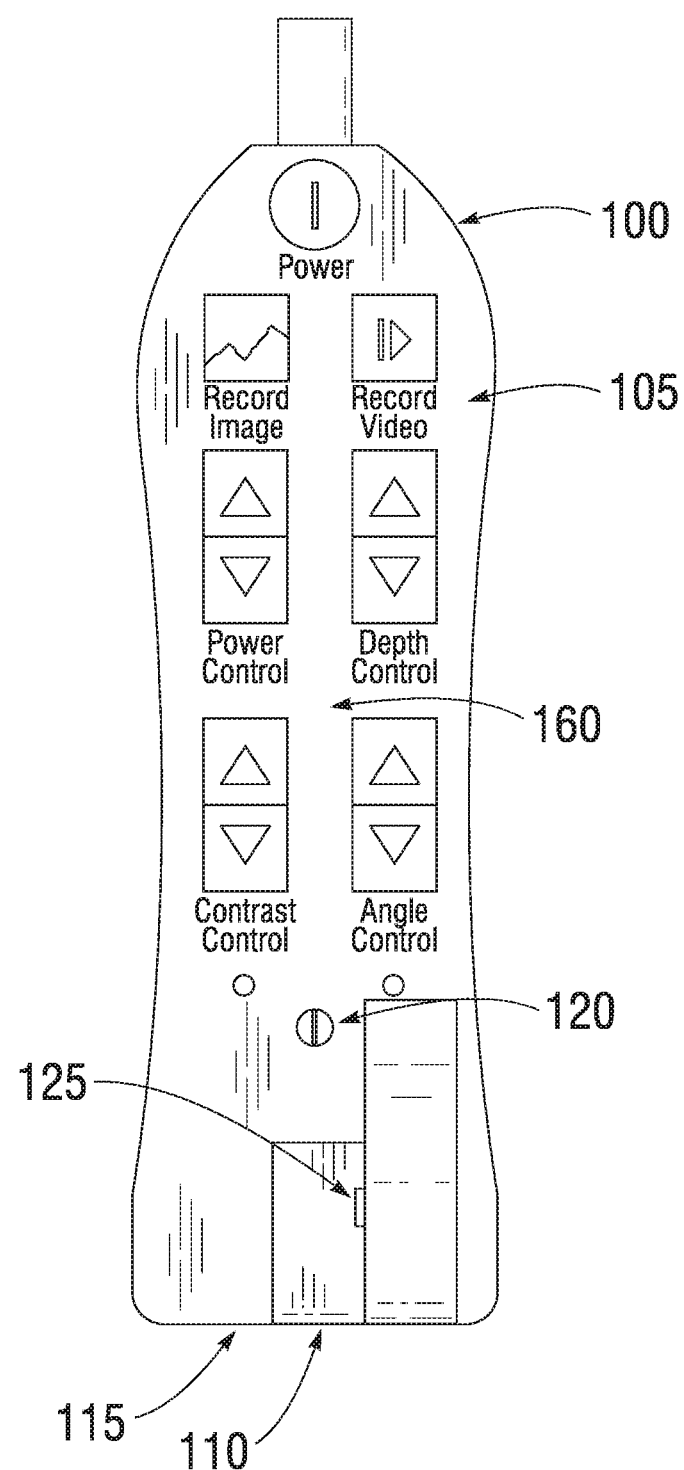
FIG. 2 is a front elevational view of an ultrasound probe in accordance with one embodiment of the present invention.
Figure 3:
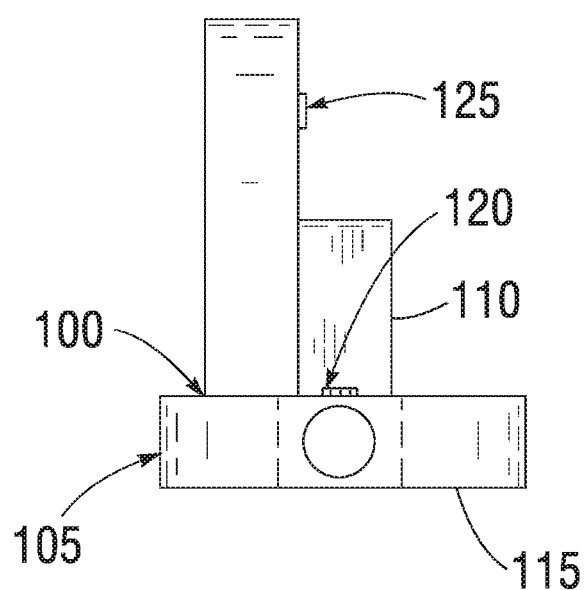
FIG. 3 is a top plan view of an ultrasound probe in accordance with one embodiment of the present invention.
Figure 4:
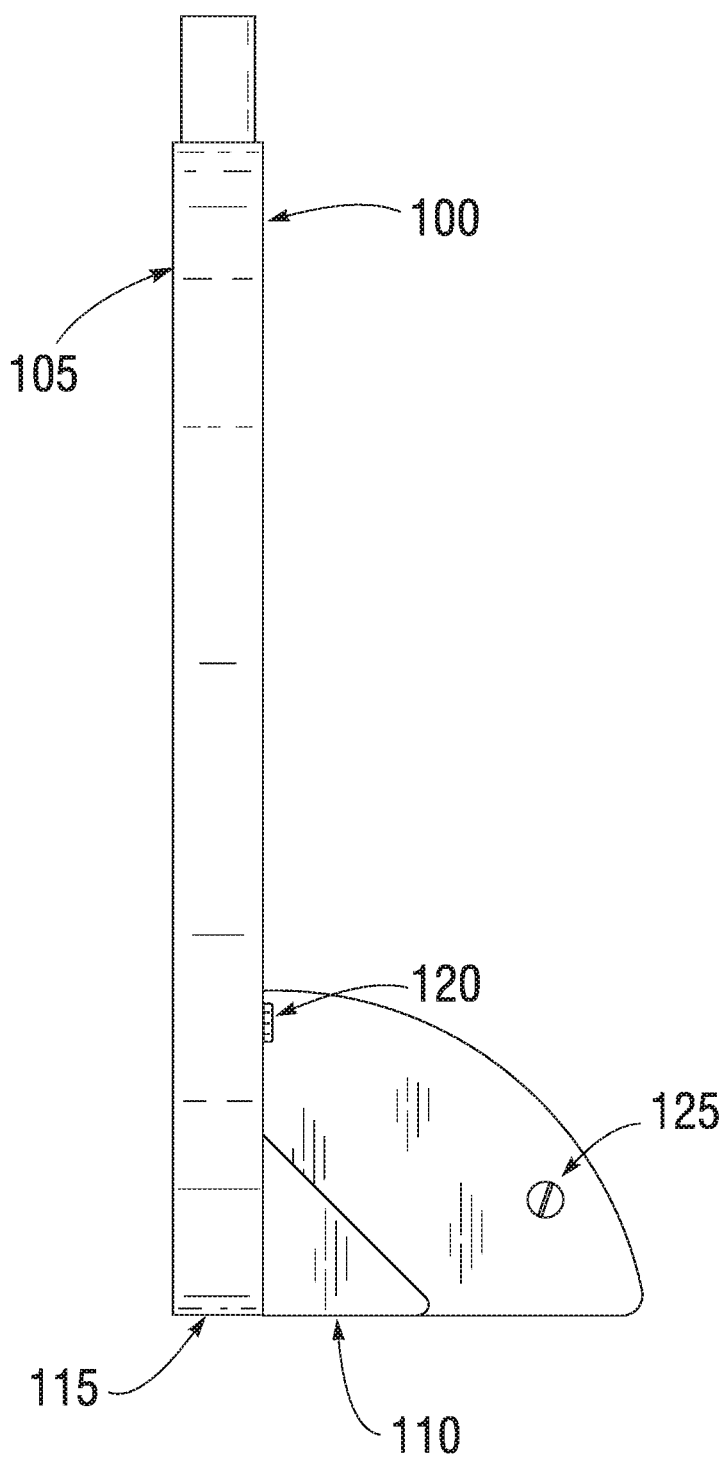
FIG. 4 is a left elevational view of an ultrasound probe in accordance with one embodiment of the present invention.
Figure 5:
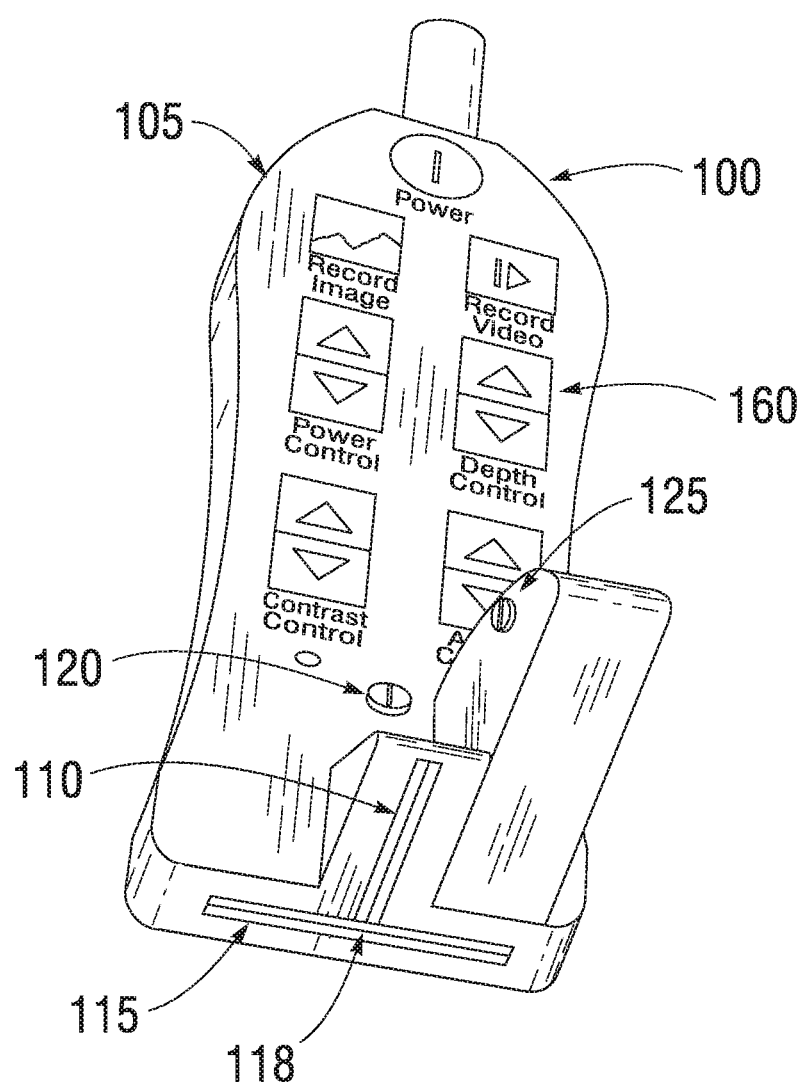
FIG. 5 is a bottom-left perspective view of an ultrasound probe in accordance with one embodiment of the present invention.
Figure 6:
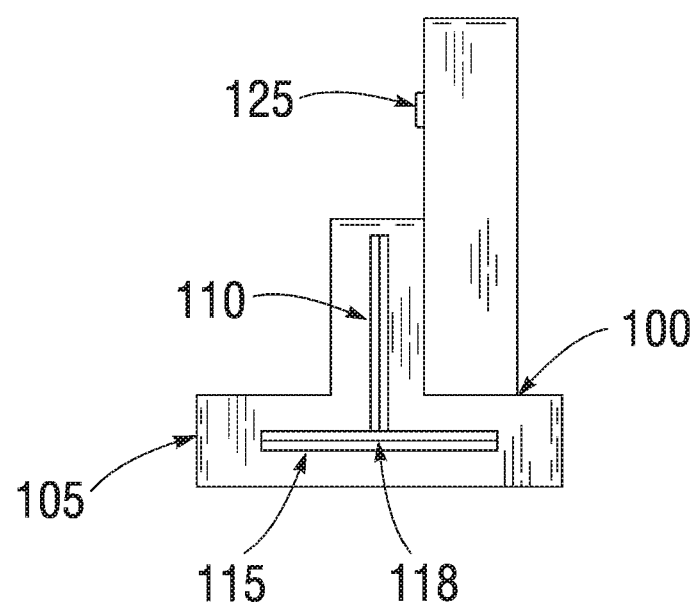
FIG. 6 is a bottom plan view of an ultrasound probe in accordance with one embodiment of the present invention.
Figure 7:
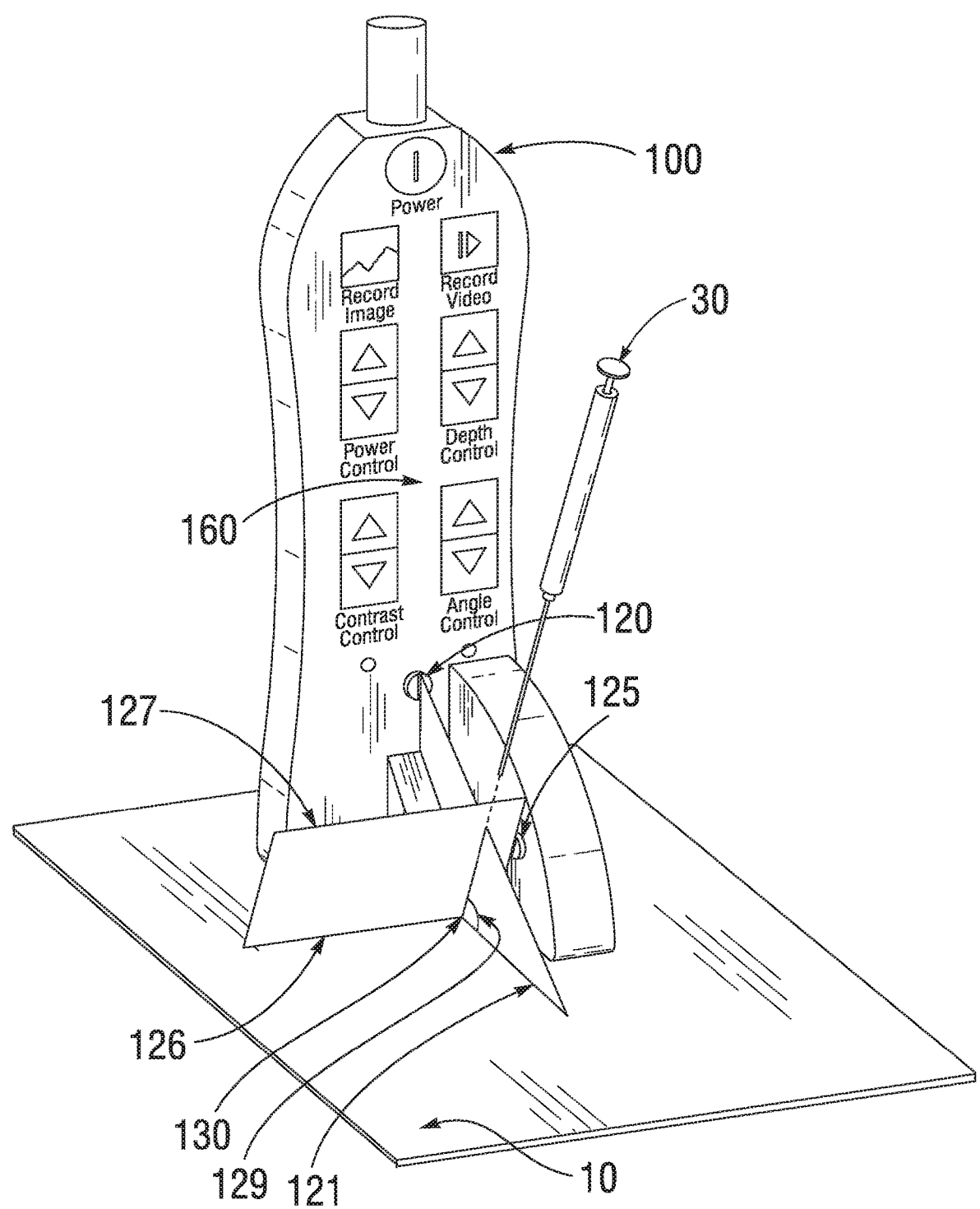
FIG. 7 is a top-left perspective view of an ultrasound probe in use in accordance with one embodiment of the present invention, the ultrasound probe directing an instrument toward a surface.
Figure 8:
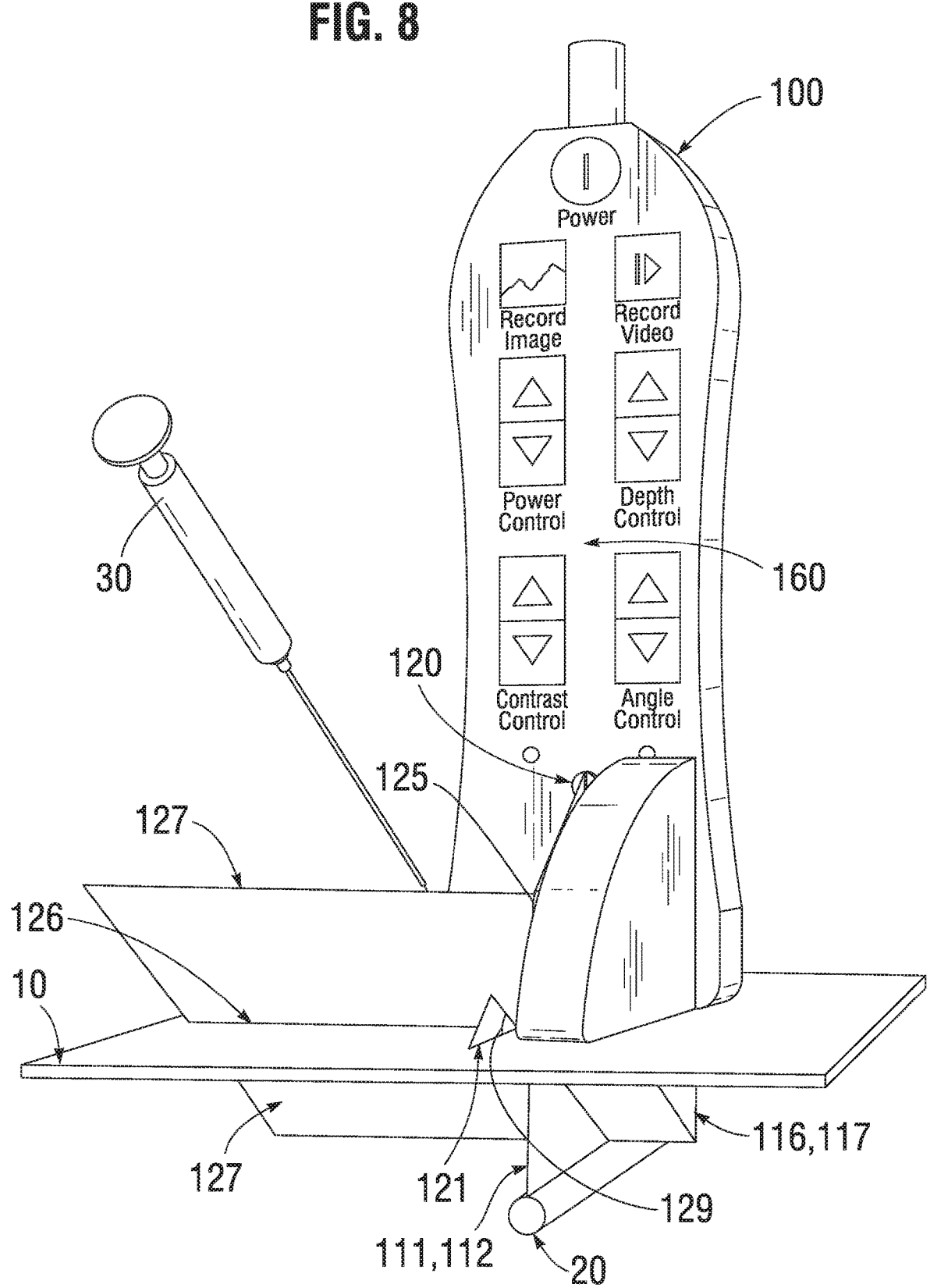
FIG. 8 is a front-right perspective view of an ultrasound probe in use in accordance with one embodiment of the present invention, the ultrasound probe directing an instrument toward a target structure beneath a surface.
Figure 9:
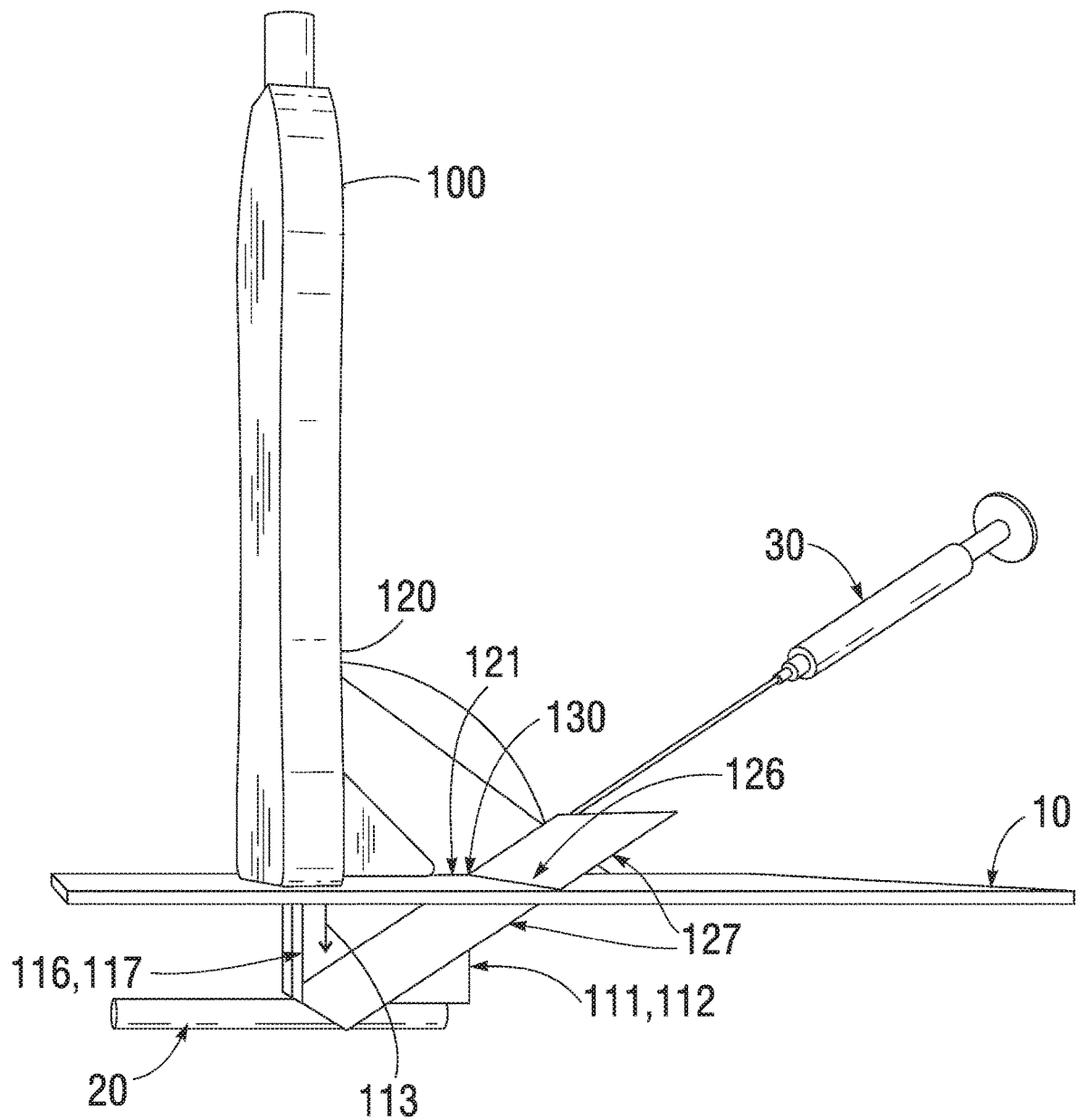
FIG. 9 is a left-back perspective view of an ultrasound probe in in use accordance with one embodiment of the present invention, the ultrasound probe directing an instrument toward a target structure beneath a surface.

With reference now to FIGS. 1-6 of the illustrative drawings, there is shown an ultrasound probe 100 in accordance with embodiments of the invention. In one embodiment, the ultrasound probe includes a housing 105, a first ultrasonic transducer array 110, a second ultrasonic transducer array 115, a first light source 120, and a second light source 125.

In one embodiment, the first ultrasonic transducer array 110 and the second ultrasonic transducer array 115 are enclosed within the housing 105, either directly or indirectly, and are substantially perpendicular to each other. In an additional embodiment, the ultrasonic transducer arrays are arranged in a T-shaped configuration. In a further embodiment, the ultrasonic transducer arrays can be configured in a biplane linear, multiplane, or 3D configuration. In another embodiment, the ultrasonic transducer arrays are configured as linear sequential arrays, linear phased arrays, or curved sequential arrays.

The first light source 120 and the second light source 125 are coupled to the housing 105. Each of the light sources may be a laser or any other light source capable of emitting a light line within a plane.

With reference to FIGS. 7-13, the first ultrasonic transducer array 110 is configured to emit a first planar ultrasonic beam 111 in a first direction 113 within a first plane 112. The second ultrasonic transducer array 115 is configured to emit a second planar ultrasonic beam 116 in the first direction within a second plane 117. The second plane is substantially perpendicular to the first plane. In one embodiment, the first and second planar ultrasonic beams may be swept ultrasonic beams.

The first light source 120 is configured to project a first light line 121 substantially within the first plane. The second light source 125 is configured to project a second light line 126 within a third plane 127. The third plane is substantially perpendicular to the first plane and intersects the second plane at an oblique angle 128. The first light line intersects and is substantially perpendicular to the second light line.

The ultrasonic transducer arrays 110, 115 permit a user to visualize a target structure 20 beneath a surface 10. For example, the ultrasound probe 100 may be placed on a patient's skin so as to emit the planar ultrasonic beams 111, 116 through the skin toward a vein beneath the skin. As is well understood by a person of ordinary skill in the art, the transducer arrays are configured to collect reflected ultrasound waves and convert those sound waves into signals that can be used to produce images of the area beneath the transducer arrays.

Figure 14:
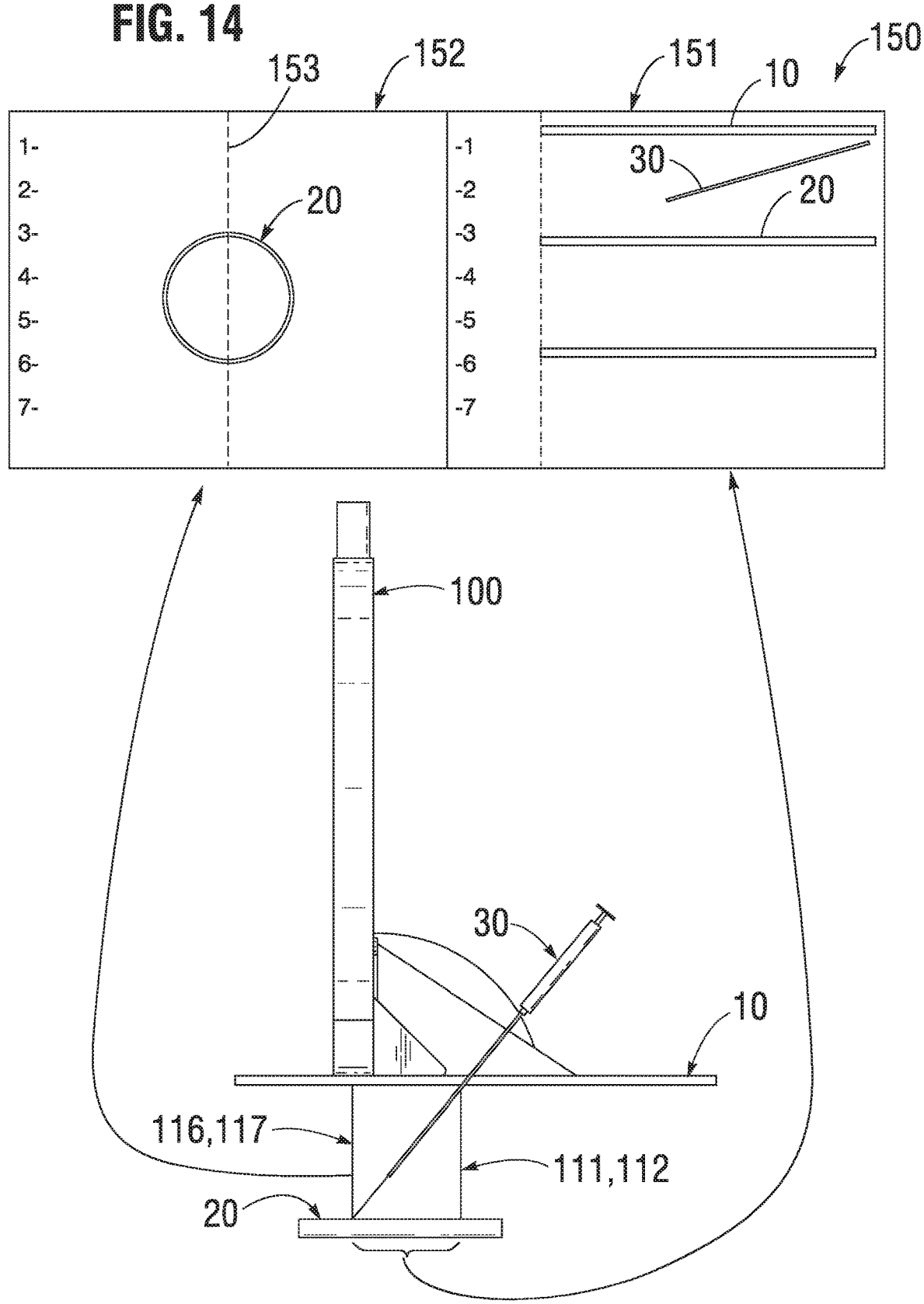
FIG. 14 is a view of an ultrasound probe and a screen in use to direct an instrument toward a target structure beneath a surface in accordance with one embodiment of the present invention.

With reference to FIG. 14, in one embodiment, a screen 150 is coupled to the ultrasound probe 100 and configured to display both a first image 151 from the first ultrasonic transducer array 110 and a second image 152 from the second ultrasonic transducer array 115. In an additional embodiment, the screen is configured to display a centerline 153. In one embodiment, the centerline corresponds to a center 118 (FIGS. 5 and 6) of the second ultrasonic transducer array. In another embodiment, the centerline corresponds to a point of intersection between the first ultrasonic transducer array and the second ultrasonic transducer array. The screen may be coupled to the ultrasound probe directly or indirectly. For example, the screen may be coupled to the ultrasound probe via a WiFi radio, Bluetooth, Ethernet, USB, or other wired or wireless connection means.

Because the first and second ultrasound transducer arrays 110 and 115 are configured to emit planar ultrasonic beams 111, 116 in the same direction and within orthogonal planes, the ultrasound probe 100 can be positioned on the surface 10 to provide simultaneous, longitudinal and transverse images of the target structure beneath the surface. In one embodiment, the longitudinal image is the first image 151, which is produced by the first ultrasonic transducer array 110 and the transverse image is the second image 152, which is produced by the second ultrasonic transducer array 115.

In use, this arrangement can permit a user to visualize the target structure 20 and the position of an instrument 30, such as a needle, in relation to the target structure. More particularly, the first and second images 151, 152 and the optional centerline 153 can be used to facilitate locating the target structure and following the instrument as it travels beneath the surface toward the target structure.

For example, it can be difficult to obtain and maintain a longitudinal image of small arteries and nerves while it is relatively easy to obtain and maintain a transverse image of these small structures. The combination of the two images allows an operator to use the transverse image as a tool to adjust the position of the ultrasound probe so as to maintain a substantial length of the small artery or nerve within the longitudinal image. More particularly, the operator can adjust the position of the ultrasound probe 100 over the target structure 20 such that the centerline 153 of the transverse image is substantially centered over the target structure. Because, in one embodiment, the centerline corresponds to a point of intersection between the first ultrasonic transducer array 110 and the second ultrasonic transducer array 115, at least part of the target structure should be visible within the longitudinal image closest to the transverse image. To finish alignment, the operator can pivot the ultrasound probe so that a substantial length of the target structure is visible within the longitudinal image.

With the ultrasound probe 100 so aligned over the target structure 20, the first and second light lines 121, 126 can be used as visual guides to direct the instrument 30 from the surface 10 to the target structure 20 beneath the surface. For example, when the first planar ultrasonic beam 111 is aligned with the target structure, the first light line 121 defines a guide path 121 for the instrument because it is substantially within the first plane 112 of the first planar ultrasonic beam.

Similarly, the third plane 127 can be configured to define an angle of entry 129 for the instrument 30, and the intersection 130 between the second light line 126 and the first light line 121 can define a point of entry 130 for the instrument. As discussed above, the second light line is projected within the third plane, which intersects the second plane 117 of the second planar ultrasonic beam 116 at an oblique angle 128. If the third plane intersects the second plane substantially at the point where the second plane intersects the target structure 20, the third plane will define an angle of entry for the instrument 129.

With the ultrasonic probe so positioned and configured, the operator can align an end of the instrument 30 with the point of entry 130, align a length of the instrument with both the guide path 121 and the angle of entry 129, and guide the instrument through the point of entry toward the target structure 20 beneath the surface 10 while substantially maintaining alignment of the length of the instrument with both the guide path and the angle of entry. In this way, the ultrasound probe 100 can be used to direct an instrument from the surface to the target structure beneath the surface such that the instrument reaches the target structure substantially at the intersection of the first and second planar ultrasonic beams 111, 116.

Of course, with different target structures at different depths beneath the surface (e.g., FIGS. 10 and 11), the third plane 127 may need to be adjusted so that it intersects the second plane 117 substantially at the point where the second plane intersects the target structure 20. Accordingly, in some embodiments, the second light source 125 may be rotated or moved, relative to the first light source 120, so as to modify the location or orientation of the third plane and the second light line 126 within that plane.

Figure 10:
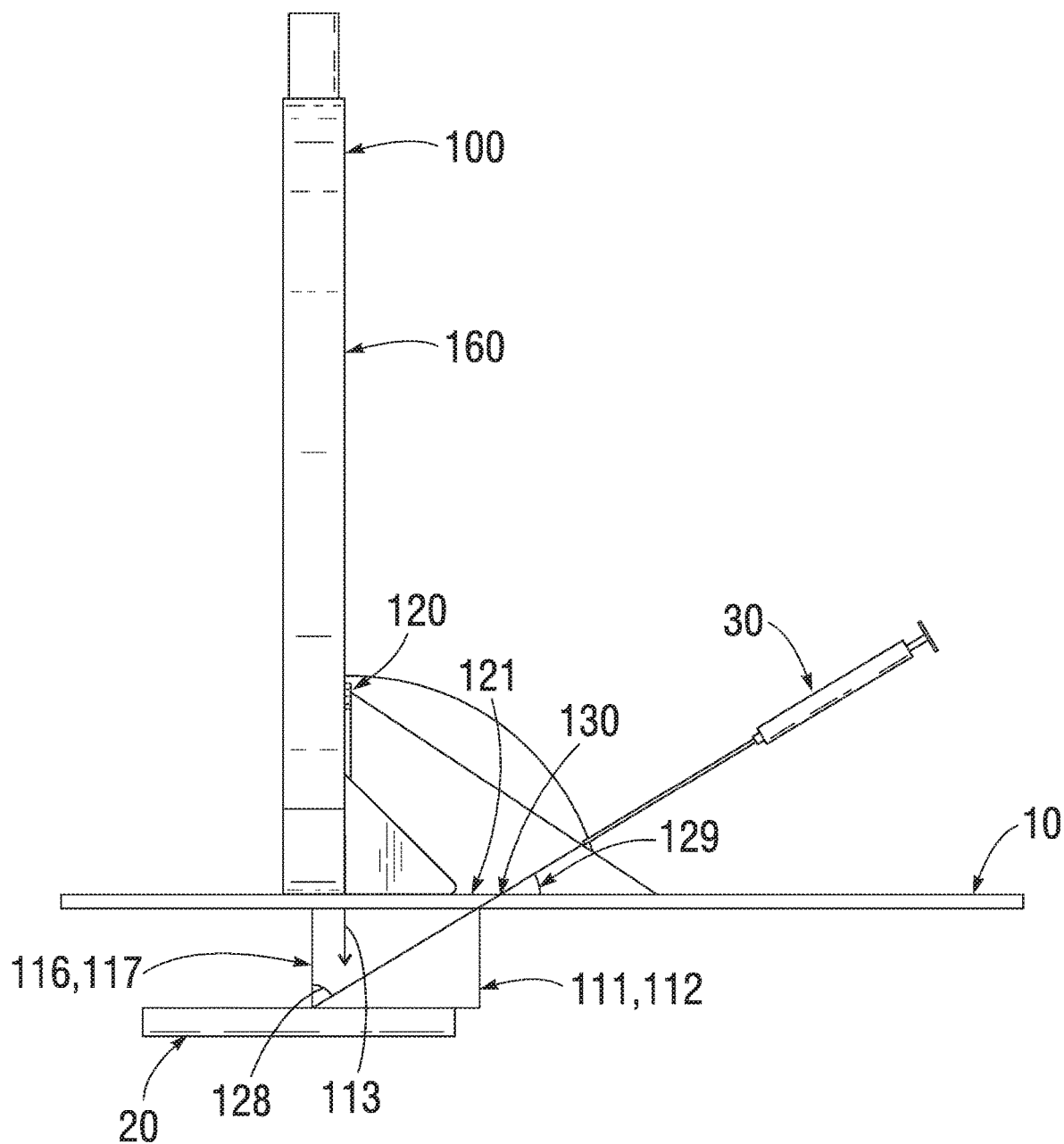
FIG. 10 is a left side elevational view of an ultrasound probe in use in accordance with one embodiment of the present invention, the ultrasound probe directing an instrument toward a target structure beneath a surface at a first angle.
Figure 11:
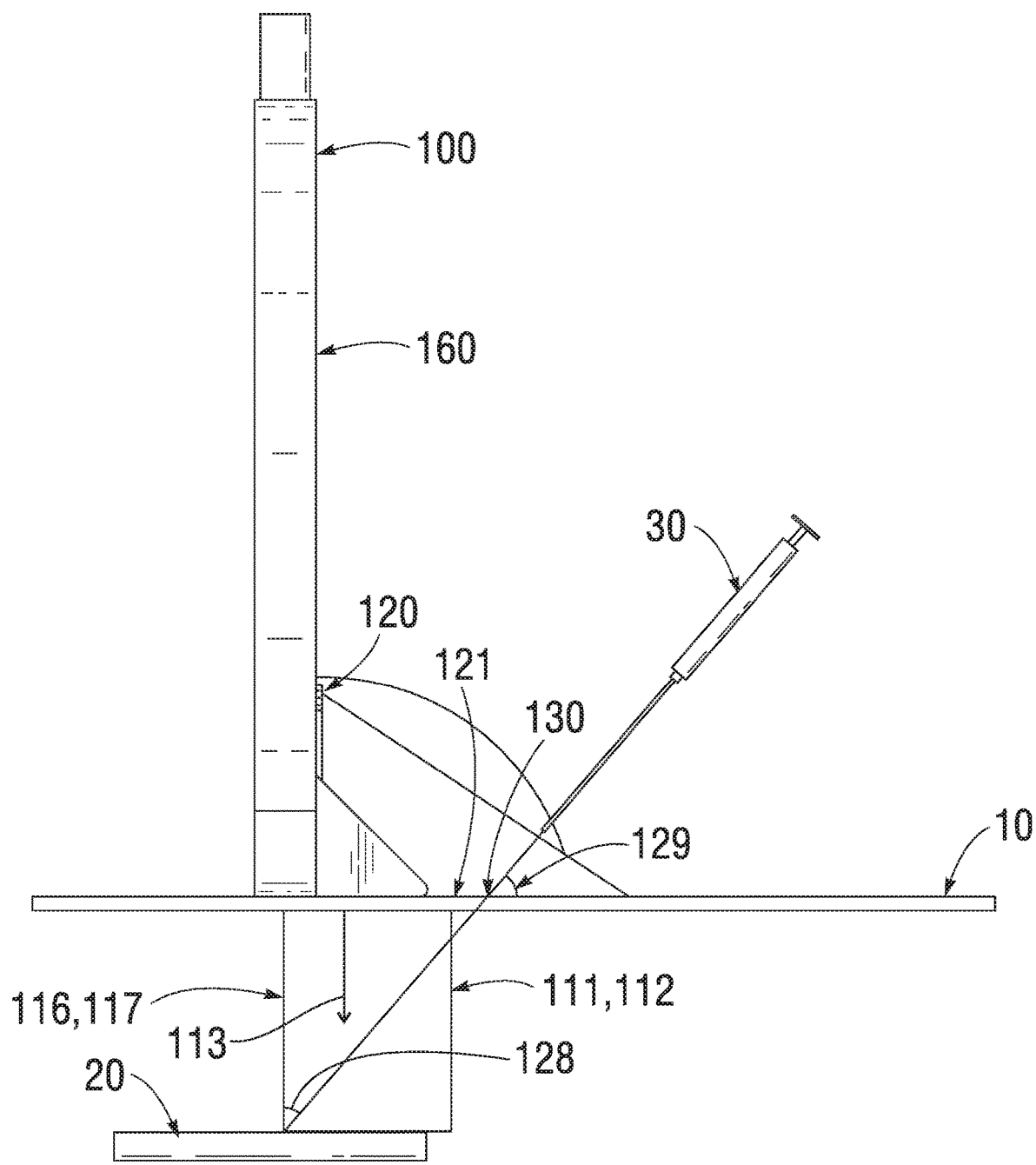
FIG. 11 is a left side elevational view of an ultrasound probe in use in accordance with one embodiment of the present invention, the ultrasound probe directing an instrument toward a target structure beneath a surface at a second angle.
Figure 12:
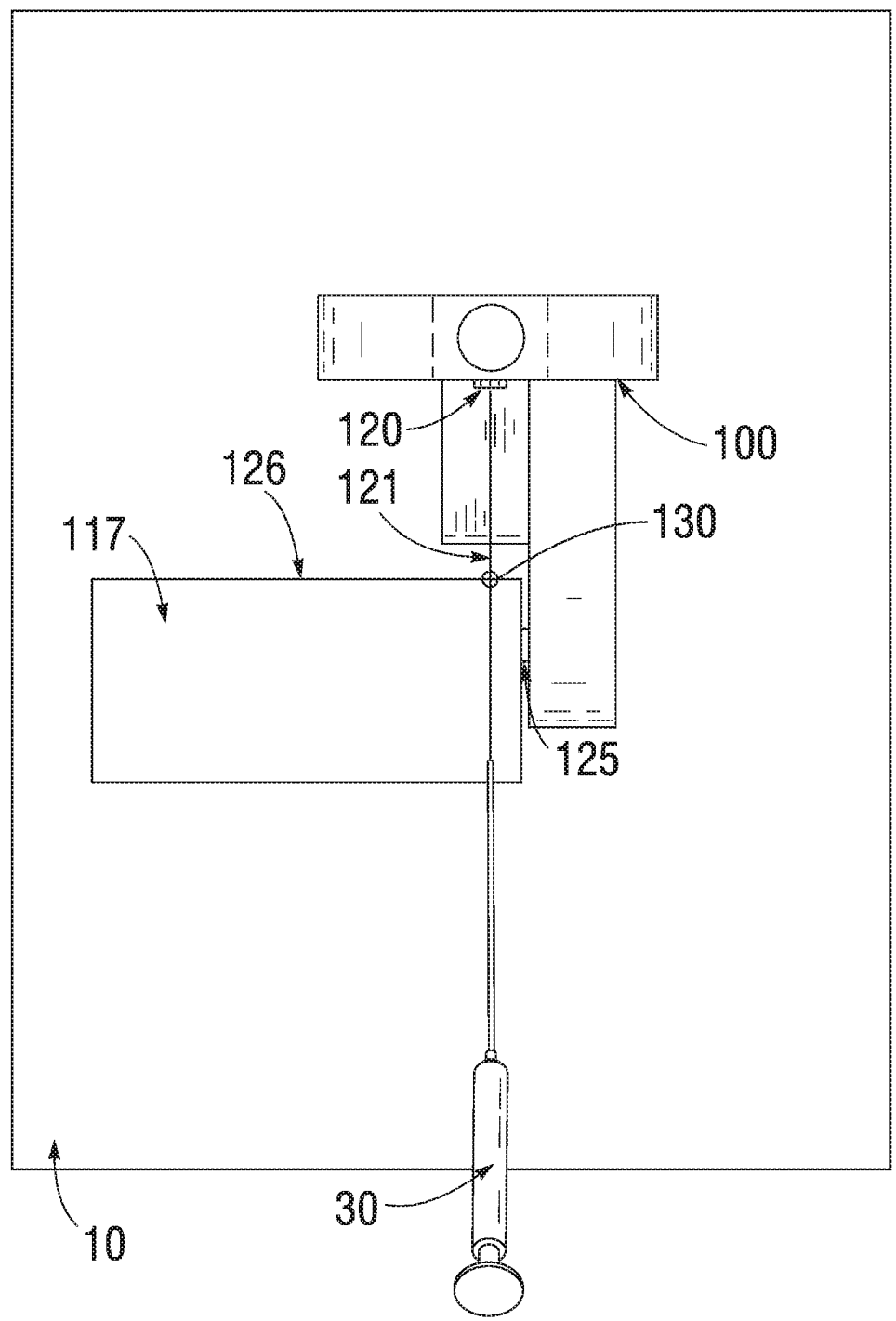
FIG. 12 is a top plan view of an ultrasound probe in use in accordance with one embodiment of the present invention, the ultrasound probe directing an instrument toward a surface.

With reference again to FIGS. 7-13, in one embodiment, the second light source 125 is configured to project the second light line 126 within the third plane 127 at a projection angle 129, wherein the projection angle is less than 90°. In an additional embodiment, a stepper motor (not shown) is coupled to the second light source. The stepper motor may be coupled to the second light source directly or indirectly. With particular reference to FIGS. 10 and 11, in a further embodiment, the stepper motor is configured to rotate the second light source and thereby adjust the projection angle, wherein the adjusted projection angle is less than 90°.

Figure 13:
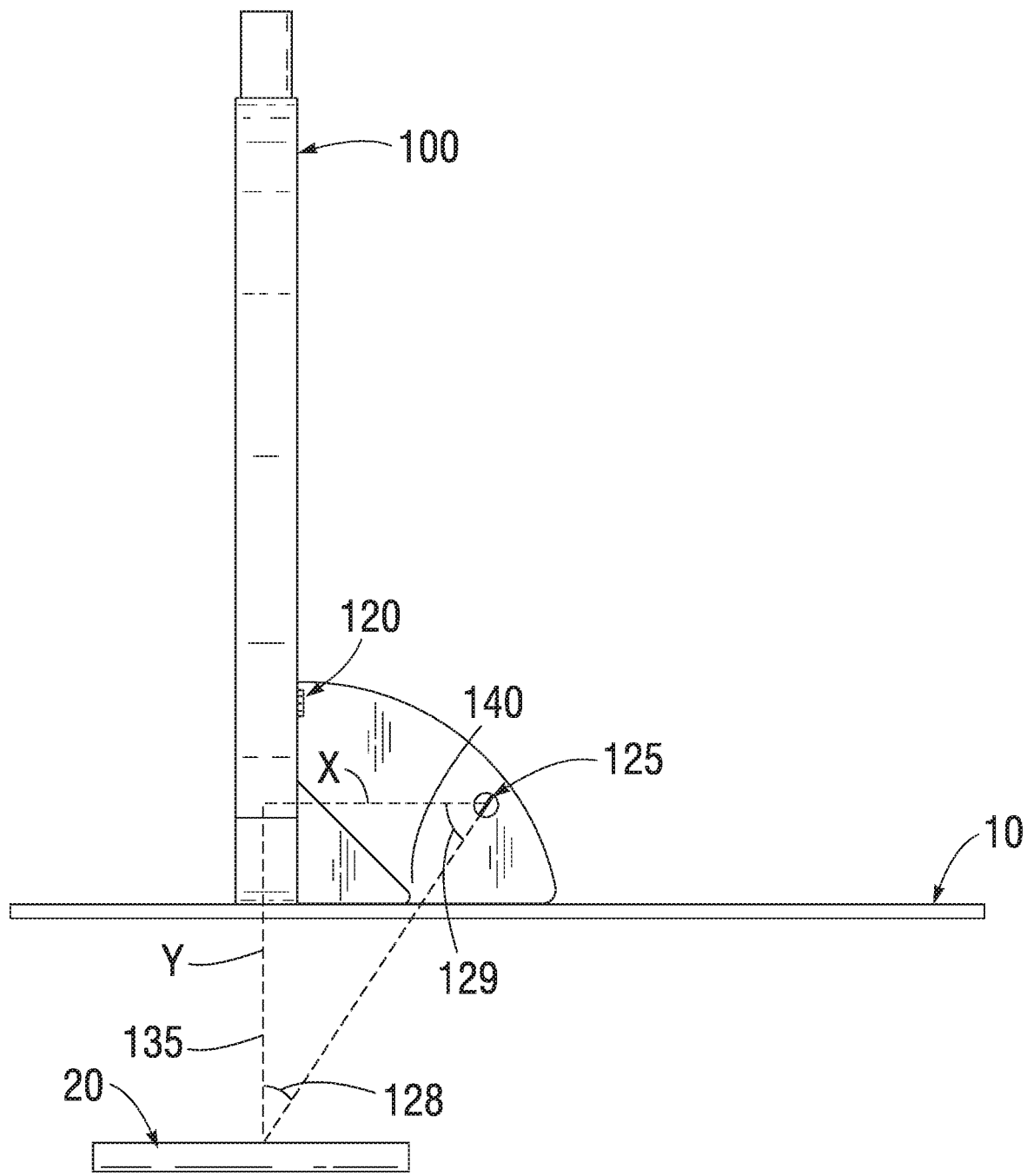
FIG. 13 is a left side elevational view of an ultrasound probe in accordance with one embodiment of the present invention, showing the ultrasound probe on a surface in relation to a target structure.

With reference to FIG. 13, the projection angle 129 (or angle of entry), is defined by the equation $\alpha=\arctan(y/x)$, where $\alpha$ is the projection angle, y is the vertical distance 135 between the target structure 20 and the second light source 125, and x is the horizontal distance 140 between the target structure and the second light source.

In yet another embodiment, a position of the second light source 125, relative to the first light source 120, is adjustable. For example, the a position of the second light source may be adjustable, relative to the first light source, in a horizontal direction, a vertical direction, or both, so that the third plane 127 intersects the second plane 117 substantially at the point where the second plane intersects the target structure 20. In such a case, the position of the second light source is defined by the equation $\tan \alpha = y/x$, where $\alpha$ is the projection angle 129 of the second light source, y is the vertical distance 135 between the target structure and the second light source, and x is the horizontal distance 140 between the target structure and the second light source.

With reference again to FIG. 2, in one embodiment, the ultrasound probe 100 further includes a control panel 160, which may optionally comprise a touchscreen. In some embodiments, the control panel includes a power button, a button to record the ultrasound images, and a button to record a video of the real-time images being generated by the ultrasound probe. In another embodiment, the image power and contrast can be adjusted, as well as the depth and angle of the target structure.

In a further embodiment, the control panel can include presets for different procedures or individuals. These presets can be modified by individuals and stored for future recall and use. For example, one operator may prefer to access a radial artery at 30°, while another operator may prefer a steeper angle, such as 45°. In such a case, the operators would select their preferred projection angle and set this as a preset value for future procedures.

Figure 15:
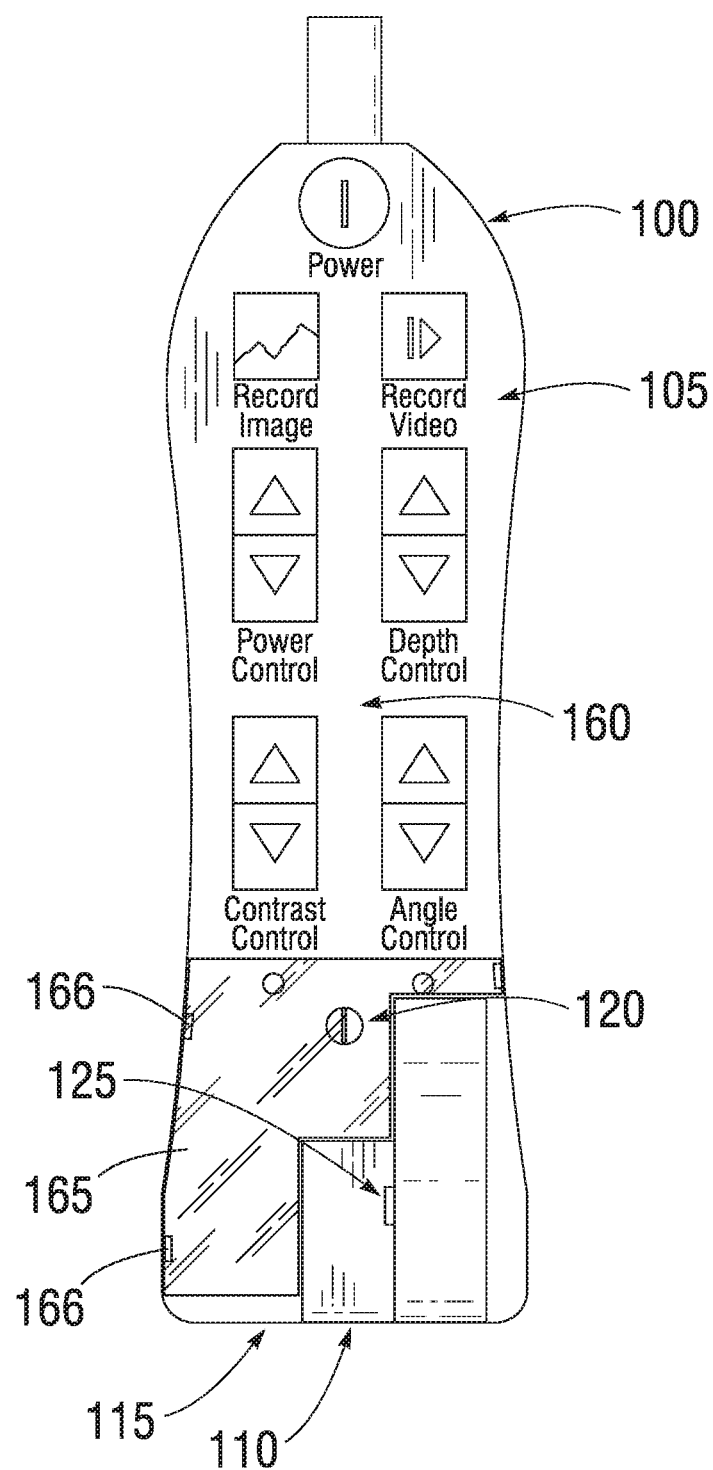
FIG. 15 is a front elevational view of an ultrasound probe with a sterile cover in accordance with one embodiment of the present invention.
Figure 16:
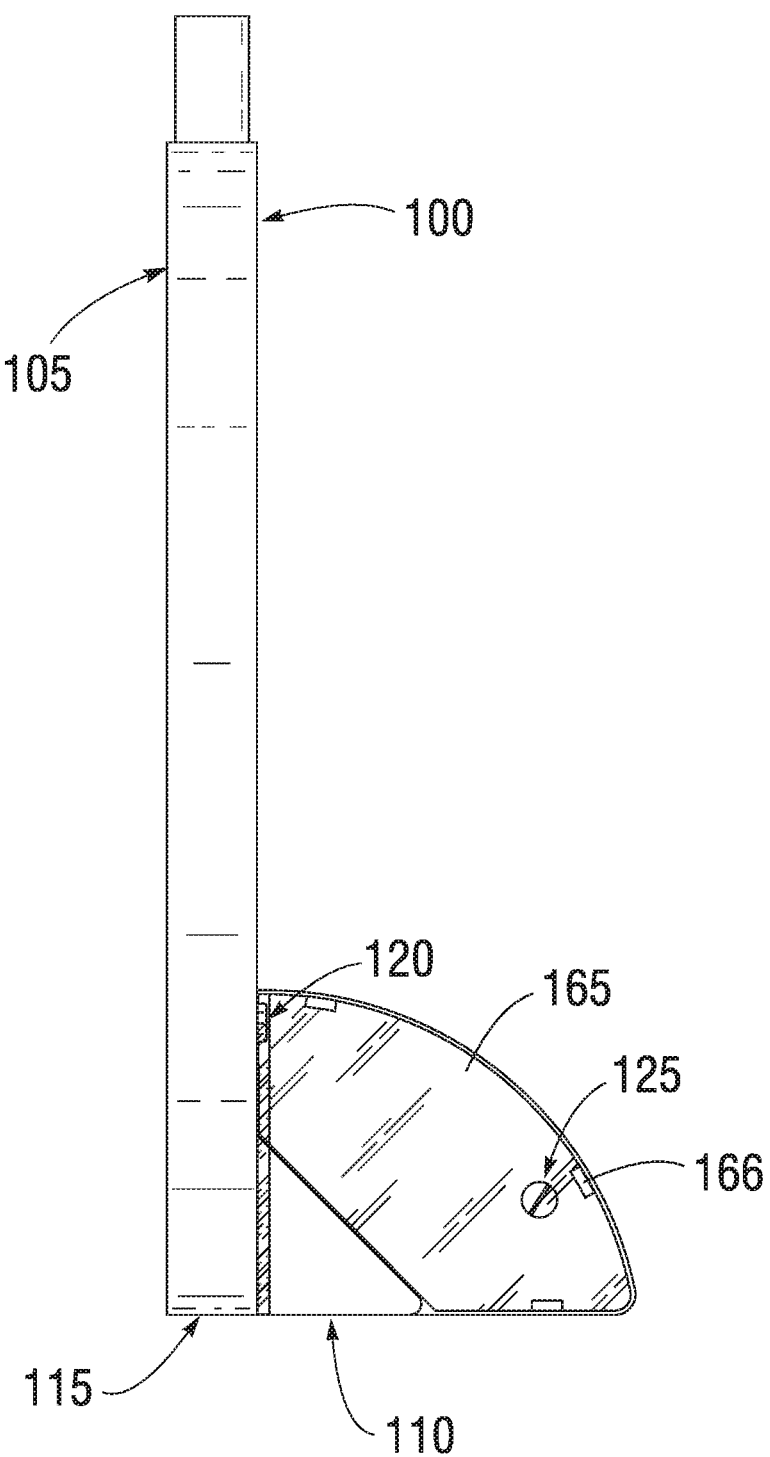
FIG. 16 is a left elevational view of an ultrasound probe with a sterile cover in accordance with one embodiment of the present invention.
Figure 17:
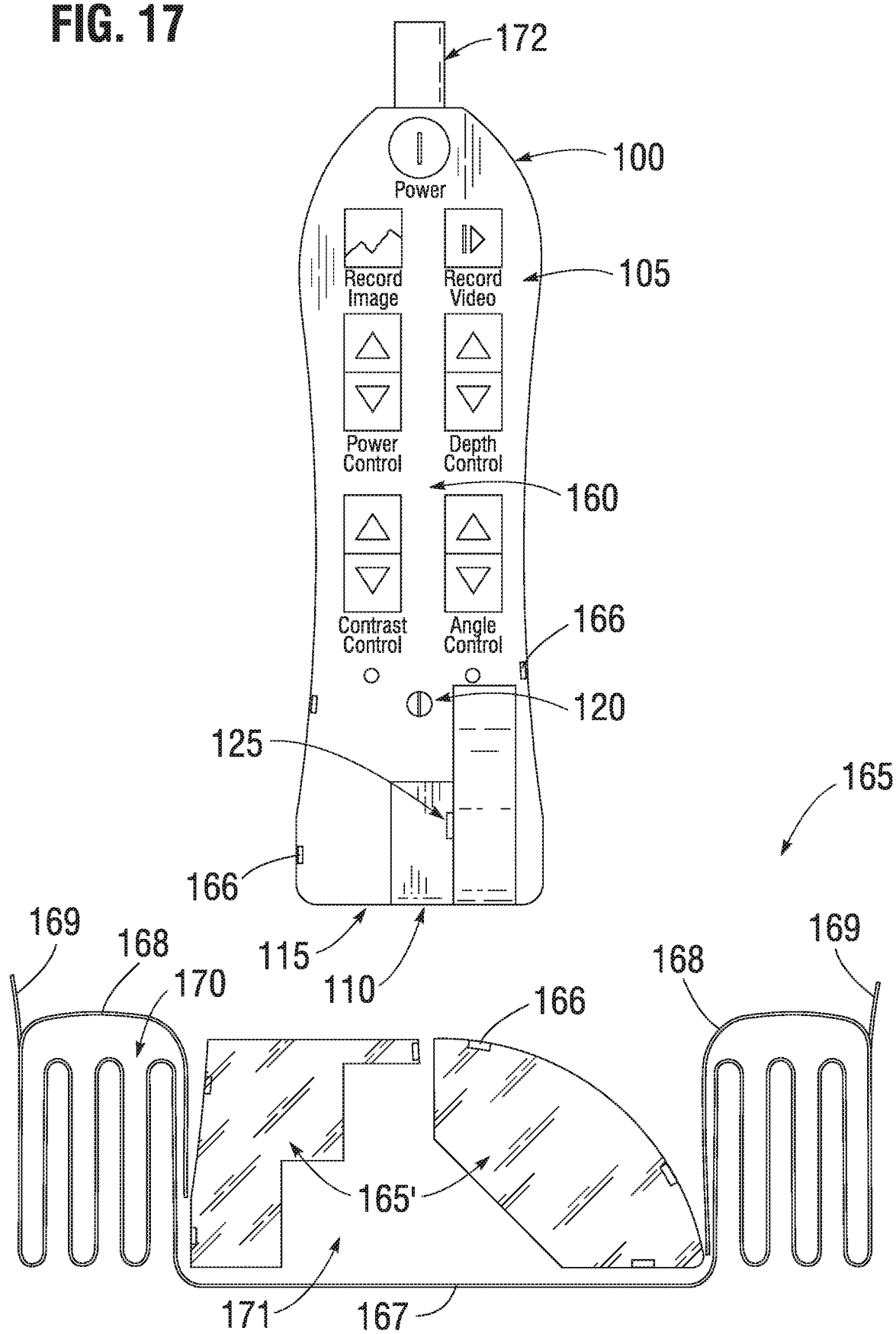
FIG. 17 is a front elevational view of an ultrasound probe and folded sterile cover, in accordance with one embodiment of the present invention, with the sides of the folded sterile cover being shown in cross-section to reveal the folds.

With reference to FIGS. 15-17, in one embodiment, the ultrasound probe 100 further comprises a sterile cover 165 coupled to the ultrasonic probe 100. In an another embodiment, an ultrasound gel can be used with the sterile probe cover 165 to optimize ultrasound transmission and optimize image quality with minimum ultrasound power. In an additional embodiment, the sterile cover 165 comprises a rigid, optically transparent material 165', such as a hard plastic, configured to be positioned over the first light source 120 and second light source 125. This rigid, optically transparent material can cover the light sources while minimizing light distortion and attenuation. As such, the rigid, optically transparent material 165' provides for a sterile environment while maintaining the desired relationship between the light lines and the planar ultrasonic beams. In an additional embodiment, the sterile cover 165 is secured to the ultrasound probe 100 by one or more attachment points 166, which may be provided on the ultrasound probe, the cover, or both.

With particular reference to FIG. 17, in one embodiment, the sterile cover 165 further comprises a flexible bag 167 coupled to at least one piece of rigid, optically transparent material 165'. In one embodiment, the rigid material 165' is heat sealed onto the flexible bag 167. The melted portion of the flexible bag will form over the rigid material a melted layer, which will not wrinkle or cause light distortion and attenuation when the light passes through it.

The flexible bag 167 can be folded over itself to create multiple fold channels 170. FIG. 17 depicts a folded flexible bag 167, in accordance with one embodiment, with the sides of the bag being shown in cross-section to reveal the fold channels 170. The rigid material 165' is visible on the front side of the center pocket 171. In one embodiment, the flexible bag further includes a guide portion 168, which extends across the top of the folded flexible bag 167, from a periphery of the flexible bag, into the center pocket 171. In an additional embodiment, the guide portion is opaque and, therefore, obscures all but the bottom of the center pocket 171 when viewed from above. Accordingly, the guide portion 168 can be configured to form a funnel leading to the center pocket 171. In this way, the guide portion facilitates placement of the ultrasonic probe 100 into the proper fold channel (i.e., center pocket 171). In yet another embodiment, the guide portion 168 further includes one or more tabs 169, which a user may pull to unfold the flexible bag 167 and draw it over the ultrasonic probe and its cable 172.

In use, an operator would add ultrasound gel to the center pocket 171, place the ultrasonic probe 100 into the center pocket, align the rigid, optically transparent members 165' over the first and second light sources 120, 125, attach the rigid members 165' to the ultrasonic probe at the attachment points 166, and pull the tabs 169 to draw the flexible bag 167 over the ultrasonic probe.

In another embodiment, the ultrasound probe further includes a sterile screen protector (not shown), which can permit an operator to interact with the ultrasound probe under sterile conditions. In one embodiment, the screen protector can be held in place by a vacuum system (not shown), which maintains and supports the screen protector in place and stretches it to enable the use of optional touch screen features. The vacuum system can be activated when the cover is placed on the screen and comes in contact with a sensor therein.

In a further embodiment, a reflective needle with depth guide is provided as the instrument 30. Ultrasound reflectivity of the needle can be enhanced to improve visualization of the needle as it approaches the target structure 20. In another embodiment, a surface of the needle includes ultrasound reflectors. In an additional embodiment, the needle is etched at regular intervals. These markings can be used to indicate the depth of the needle beneath the surface.

With reference again to FIGS. 7-14, the present invention is also embodied in a method of directing an instrument 30 from a surface 10 to a target structure 20 beneath the surface. In one embodiment, the method includes the steps of emitting a first planar ultrasonic beam 111 in a first direction 113 within a first plane 112, emitting a second planar ultrasonic beam 116 in the first direction within a second plane 117, projecting a first light line 121 substantially within the first plane, projecting a second light line 126 within a third plane 127, aligning an end of the instrument with a point of entry 130, aligning a length of the instrument with both a guide path 121 and an angle of entry 129, and guiding the instrument through the point of entry toward the target structure beneath the surface, while substantially maintaining alignment of the length of the instrument with both the guide path and the angle of entry. The second plane and the third plane are both substantially perpendicular to the first plane. The third plane intersects the second plane at an oblique angle 128 and also defines the angle of entry for the instrument. The first light line defines the guide path for the instrument. The second light line intersects and is substantially perpendicular to the first light line, and a point of intersection 130 between the first light line and the second light line defines the point of entry for the instrument.

With particular reference to FIG. 14, in one embodiment, the method includes displaying both a first image 151 from the first planar ultrasonic beam 111 and a second image 152 from the second planar ultrasonic beam 116. In another embodiment, the second image includes a centerline 153. In a further embodiment, the centerline corresponds to a center 118 of the second planar ultrasonic beam. In yet another embodiment, the centerline corresponds to a point of intersection between the first planar ultrasonic beam and the second planar ultrasonic beam.

In one embodiment, the method includes aligning the second planar ultrasonic beam 116 over the target structure 20 such that the centerline 153 of the second image 152 is substantially centered over the targets structure. In another embodiment, the method includes aligning the first planar ultrasonic beam 111 over the target structure such that the target structure is visible in the first image 151 while the centerline of the second image is substantially centered over the target structure.

In another embodiment, the method includes selecting the target structure 20 on the first or second image 151, 152. For example, the target structure can be either automatically or manually identified and a touch screen can be used to select the best path from the surface 10 to the target structure. In a further embodiment, the method includes selecting a desired angle of entry 129. In an additional embodiment, the method includes selecting a desired point of entry 130 on the first image 151. In yet another embodiment, the method includes selecting both a desired point of entry on the first image and a desired angle of entry.

With reference to FIG. 13, in one embodiment, the method includes determining both a vertical 135 and a horizontal distance 140 between the target structure 20 and a light source 125 projecting the second light line 126. In another embodiment, the method includes calculating a projection angle 129 of the light source required to project the second light line within the third plane 127 such that the third plane is substantially incident a point of intersection between the second plane 117 and the target structure. The projection angle is defined by the equation $\alpha = \arctan(y/x)$, where $\alpha$ is the projection angle, y is the vertical distance 135 between the target structure and the light source, and x is the horizontal distance 140 between the target structure and the light source. In another embodiment, the method includes rotating the light source so as to project the second light line within the third plane substantially at the calculated projection angle.

In one embodiment, the method includes calculating a position of the light source 125 required to project the second light line 126 within the third plane 127 such that the third plane is substantially incident a point of intersection between the second plane 117 and the target structure 20. The position is determined from an equation $\tan \alpha = y/x$, where $\alpha$ is a projection angle of the light source, y is the vertical distance 135 between the target structure and the light source, and x is the horizontal distance 140 between the target structure and the light source. In another embodiment, the method includes moving the light source substantially to the calculated position.

In one embodiment, the method includes the step of calculating both a projection angle 129 and a position of the light source 125 required to project the second light line 126 within the third plane 127 such that the third plane is substantially incident a point of intersection between the second plane 117 and the target structure 20. The projection angle and position are determined from an equation $\tan \alpha = y/x$, where $\alpha$ is the projection angle, y is the vertical distance 135 between the target structure and the light source, and x is the horizontal distance 140 between the target structure and the light source. In another embodiment, the method includes rotating the light source so as to project the second light line within the third plane substantially at the calculated projection angle, and moving the light source substantially to the calculated position.

It should be appreciated from the foregoing description that the present invention provides an ultrasound probe that enables heath care practitioners to safely perform procedures involving internal bodily structures with greater ease and accuracy and fewer complications. The ultrasound probe can be used to reliably and continuously direct an instrument from a surface to a target structure beneath the surface.

Specific methods, devices, and materials are described, although any methods and materials similar or equivalent to those described can be used in the practice or testing of the present embodiment. Unless defined otherwise, all technical and scientific terms used herein have the same meanings as commonly understood by one of ordinary skill in the art to which this embodiment belongs.

Without further elaboration, it is believed that one skilled in the art, using the proceeding description, can make and use the present invention to the fullest extent. The invention has been described in detail with reference only to the presently preferred embodiments. Persons skilled in the art will appreciate that various modifications can be made without departing from the invention. Accordingly, the invention is defined only by the following claims.

The invention claimed is:

1. A method of directing an instrument from a surface to a target structure beneath the surface, the method comprising the following steps:
   emitting a first planar ultrasonic beam in a first direction within a first plane;
   emitting a second planar ultrasonic beam in the first direction within a second plane, which is substantially perpendicular to the first plane;
   projecting a first light line substantially within the first plane, wherein the first light line defines a guide path for the instrument;
   projecting a second light line within a third plane, which is substantially perpendicular to the first plane and intersects the second plane at an oblique angle, wherein the second light line intersects and is substantially perpendicular to the first light line, wherein the third plane defines an angle of entry for the instrument, and wherein a point of intersection between the first light line and the second light line defines a point of entry for the instrument;
   aligning an end of the instrument with the point of entry;
   aligning a length of the instrument with both the guide path and the angle of entry; and
   guiding the instrument through the point of entry toward the target structure beneath the surface, while substantially maintaining alignment of the length of the instrument with both the guide path and the angle of entry.

2. The method of claim 1, further comprising the step of displaying both a first image from the first planar ultrasonic beam and a second image from the second planar ultrasonic beam.

3. The method of claim 2 wherein the second image includes a centerline.

4. The method of claim 3, wherein the centerline corresponds to a center of the second planar ultrasonic beam.

5. The method of claim 3, further comprising the step of aligning the second planar ultrasonic beam over the target structure such that the centerline of the second image is substantially centered over an image of the target structure.

6. The method of claim 5, further comprising the step of aligning the first planar ultrasonic beam over the target structure such that the target structure is visible in the first image while the centerline of the second image is substantially centered over the image of the target structure.

7. The method of claim 6, further comprising the step of determining both a vertical and a horizontal distance between the target structure and a light source projecting the second light line.

8. The method of claim 7, further comprising the step of selecting the target structure on the first or second image.

9. The method of claim 8, further comprising the step of selecting a desired angle of entry.

10. The method of claim 8, further comprising the step of selecting a desired point of entry on the first image.

11. The method of claim 7, further comprising the step of calculating a projection angle of the light source required to project the second light line within the third plane such that the third plane is substantially incident a point of intersection between the second plane and the target structure.

12. The method of claim 11, further comprising the step of rotating the light source so as to project the second light line within the third plane substantially at the calculated projection angle.

13. The method of claim 7, further comprising the step of calculating a position of the light source required to project the second light line within the third plane such that the third plane is substantially incident a point of intersection between the second plane and the target structure.

14. The method of claim 13, further comprising the step of moving the light source substantially to the calculated position.

15. The method of claim 7, further comprising the step of calculating both a projection angle and a position of the light source required to project the second light line within the third plane such that the third plane is substantially incident a point of intersection between the second plane and the target structure.

16. The method of claim 15, further comprising the steps of rotating the light source so as to project the second light line within the third plane substantially at the calculated projection angle, and moving the light source substantially to the calculated position.

* * * * *